United States Patent [19]

Sitte

[11] Patent Number: 4,580,416
[45] Date of Patent: Apr. 8, 1986

[54] APPARATUS FOR THE CRYOFIXATION OF SPECIMENS

[75] Inventor: Hellmuth Sitte, Siefeld/Triol, Austria

[73] Assignee: C. Reichert Optische Werke, AG, Vienna, Austria

[21] Appl. No.: 730,530

[22] Filed: May 6, 1985

[30] Foreign Application Priority Data

May 7, 1984 [DE] Fed. Rep. of Germany ....... 3416789

[51] Int. Cl.$^4$ ............................................. F25B 19/00
[52] U.S. Cl. ..................................... 62/514 R; 62/383
[58] Field of Search .................. 62/383, 49, 514 R, 78

[56] References Cited

U.S. PATENT DOCUMENTS 4,302,950 12/1981 Sitte ........................................ 62/78
4,332,532 11/1980 Marsh ................................... 62/383

Primary Examiner—Ronald C. Capossela
Attorney, Agent, or Firm—Alan H. Spencer; S. Raines

[57] ABSTRACT

Apparatus for the cryofixation of biological, medical or technical specimens having a high water content or fluid content by immersion in a cooling bath or on a metal mirror surface, comprises a container for coolant within which is disposed in a tank for specimen cooling medium. An injector is provided for holding a specimen and moving it along a delivery path. A member having a mirror surface is provided for mirror surface cryofixation, said member being adapted to be removably disposed at a position located in the injection path. A highly thermally conductive contact is provided between the tank and the member.

15 Claims, 6 Drawing Figures

APPARATUS FOR THE CRYOFIXATION OF SPECIMENS

BACKGROUND OF THE INVENTION

This invention relates to apparatus for the cryofixation of specimens particularly biological, medical or technical specimens having a high water or fluid content.

Two methods are currently favoured in the cryofixation (rapid freezing) of specimens having a high liquid content, such as biological or medical specimens, gels and suspensions, for photo-examination, particularly for electron microscope examinations. These are immersion cryofixation, in which the specimen is immersed in a cooling bath, and metal mirror cryofixation, in which the specimen is applied against a highly polished metal surface. In both cases it is important to withdraw the greatest possible quantity of heat from the specimen within the shortest time, in order that any segregation of the aqueous or liquid mixture phases is reduced to a minimum.

In this respect, neither of these two methods is ideal for all known specimens and for all known subsequent preparations. For example, immersion cryofixation is excellently suited for freezing thin "sandwich" preparations and ultra-fine liquid films in grid meshes (the bare grid method), for which the metal mirror system is unserviceable.

On the other hand, by impacting animal or vegetable organs and tissues against a deeply cooled metal mirror, optimally plane surfaces are obtained, since the existing surface relief is considerably flattened by the impact. Surfaces produced on the metal mirror are therefore ideally suited for the subsequent preparation of sections on the cryo-ultramicrotome, whereas after immersion cryofixation tissues are only suitable for such use with substantial limitations.

It is therefore extremely inconvenient and costly in practical work, that in the majority of cases two different expensive instruments are required which must, in many respects, include similar parts for cooling, for the measurement and regulation of temperature, for the injection of specimens and for the subsequent cryo-transfer of the frozen specimens to an electron microscope or to apparatus for further processing, such as subsequent preparation in freeze-breaking and freeze-etching equipment, a cryo-substitution system or a cryo-ultramicrotome.

SUMMARY OF THE INVENTION

It is accordingly an object of the present invention to provide a universal apparatus for immersion and metal mirror cryofixation by means of which specimens of the above types may be frozen either on the metal mirror surface or in a cooling bath without the need for complicated conversion steps, and without the production costs of the basic appliance being increased or its structural design being unduly complicated.

According to the present invention there is provided apparatus for the cryofixation of specimens, comprising a container for a coolant; a tank for a specimen cooling medium, said tank being disposed within said container; an injector for holding a specimen and moving it along a delivery path; and a member having a mirror surface; wherein said member is adapted to be removably disposed at a position located in the delivery path, and a highly thermally conductive contact is provided between the tank and the member.

The tank is preferably metallic and may be constructed so that the member having the mirror surface can be attached to it easily and with good thermal contact between the member and the tank. Normally the member would be metallic having a metal mirror surface.

In this manner it is possible to utilize the apparatus for cryofixation alternatively by immersion or on the metal mirror surface, without the need to purchase and set up two complicated items of equipment for this purpose. This not only saves capital costs, but also economises on space occupied in the laboratory. Personnel dealing with the apparatus need to be trained only on a single system.

In a preferred embodiment of the invention the member comprises a carrier and an exchangeable mirror element of smaller dimensions which can be inserted into or placed upon the carrier; the carrier may be releasably securable to the cooling bath tank. The metal mirror surface may be formed on the surface of the mirror element. This further embodiment permits used mirror surfaces to be rapidly exchanged and also to be particularly simply cleansed and repolished. This embodiment also enables metal mirrors to be produced from expensive materials that may be particularly suitable, or to be provided with expensive coatings that may be particularly suitable.

In another advantageous embodiment of the invention, the carrier for the metal mirror is of precisely the same geometrical shape as the tank for the specimen cooling medium, generally a cylinder, so that the metal mirror carrier takes the place of the cooling bath. This enables the systems to be operated virtually identically, and provides in particular for absolutely reproducible temperature adjustment and temperature measurement for both the methods and a simple change from the one method to the other.

The specimen cooling medium may be a cryogenic refrigerant medium such as propane, ethane or halogenated hydrocarbons.

In another advantageous further embodiment of the invention, the mirror surface is rotatable about a vertical axis which is parallel and eccentric to the axis of the injector and/or to the delivery path of the specimen during injection. By this means it is a simple matter to rotate the mirror after one completed cryofixation to make another previously unused section of the mirror surface available for a subsequent cryofixation.

BRIEF DESCRIPTION OF THE DRAWINGS

Reference is now made to the accompanying drawings, in which.

DESCRIPTION OF THE PREFERRED EMBODIMENTS

Figure 1:
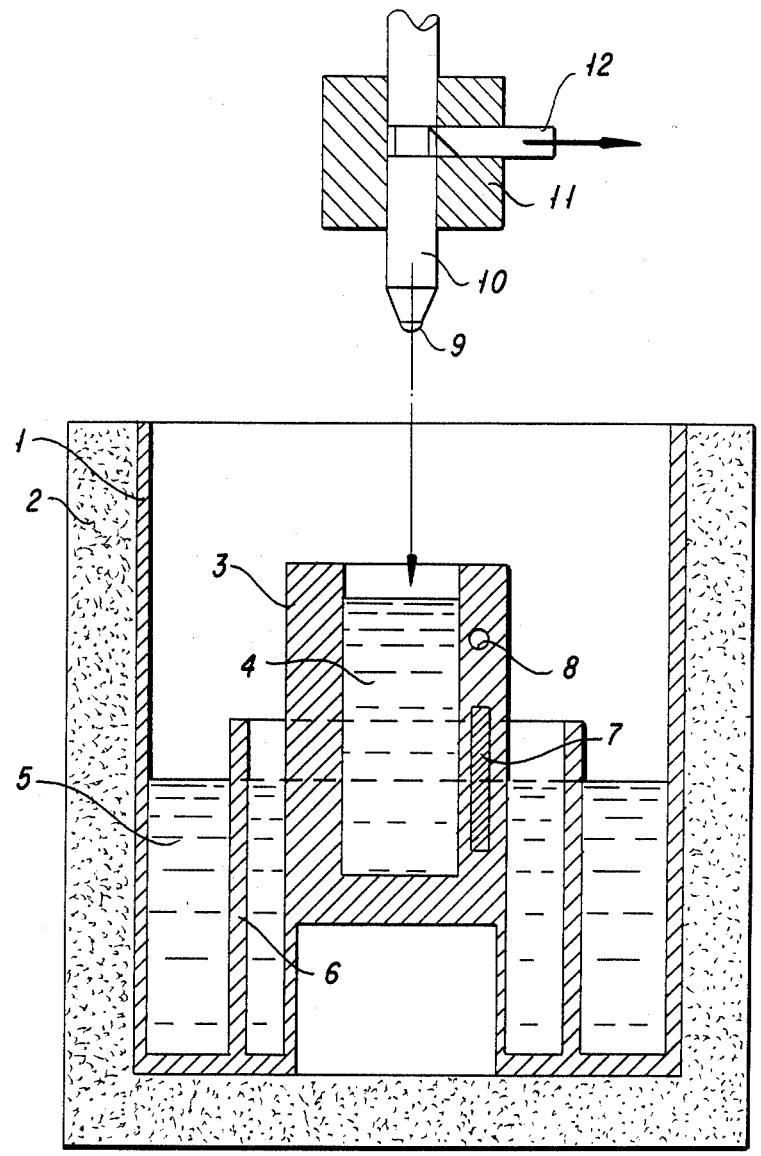
FIG. 1 is a diagrammatic cross-sectional view of apparatus for immersion cryofixation in accordance with the prior art.

In the prior art system for immersion cryofixation illustrated in FIG. 1, immersion tank 3 for the specimen cooling bath constituted by specimen cooling medium 4 is located within a container 1 surrounded by insulation 2. The tank 3 is generally cooled by means a coolant in the form of liquid nitrogen ($LN_2$) 5. In standby operation any direct contact between $LN_2$ and tank 3 is prevented by a sleeve 6. In this way it is possible, without major $LN_2$ losses, to adjust and maintain constant temperatures which are above the boiling point of the $LN_2$ 5 ($-196°$ C.), by means of a heating cartridge 7, a thermosensor 8 and a regulating electronic system (not shown). This is essential for the majority of refrigerant media 4 commonly used (for example, propane, ethane or halogenated hydrocarbons).

A specimen 9 is carried on an injector rod 10 guided accurately in an element 11. After actuation of a trigger 12, the injector rod 10 moves downwardly with the specimen 9 along a delivery path in the direction of the arrow either solely by gravity of further accelerated by spring forces or other electromechanical or pneumatic means, and the specimen 9 dips into the cooling medium 4 for cryofixation.

Figure 2:
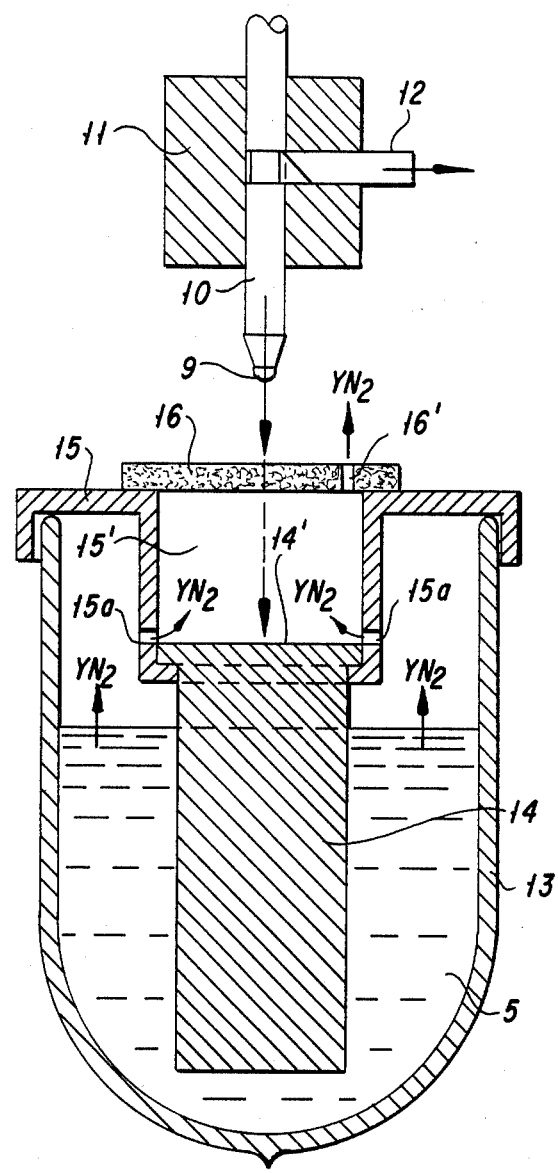
FIG. 2 is a diagrammatic cross-sectional view, analogous to FIG. 1, of apparatus for metal mirror surface cryofixation in accordance with the prior art.

An entirely different procedure is followed in the case of cryofixation on a metal mirror surface, which is illustrated in a simple prior art construction in FIG. 2. If $LN_2$ 5 is being used as cryogen, it is held in a suitable container, such as Dewar vessel 13. The $LN_2$ cools a metal block 14 down to a temperature close to $-196°$ C. The metal block 14 is supported by an insert 15, which may for example be constructed so that it encloses a cylindrical chamber 15' which can initially be closed at the top by a thermally insulating cover 16. The gaseous nitrogen ($GN_2$), denoted by arrows, fumes steadily from the $LN_2$ 5 and leaves the Dewar vessel 13 through passages 15a in the insert 15 into the chamber 15' and out of the latter through a passage 16' in the cover 16. The surface of the block 14 which forms the base of the chamber 15' is polished to a high gloss and constitutes a metal mirror surface 14'. The specimen 9 is impacted against the mirror surface 14' at considerable speed after removal of the cover 16 and actuation of the trigger 12, thereby flattening its surface relief, which is always present. By this method the structure in the outer layers of the specimen is well preserved resulting in optimum conditions for subsequent cryo-ultramicrotomy.

Figure 3:
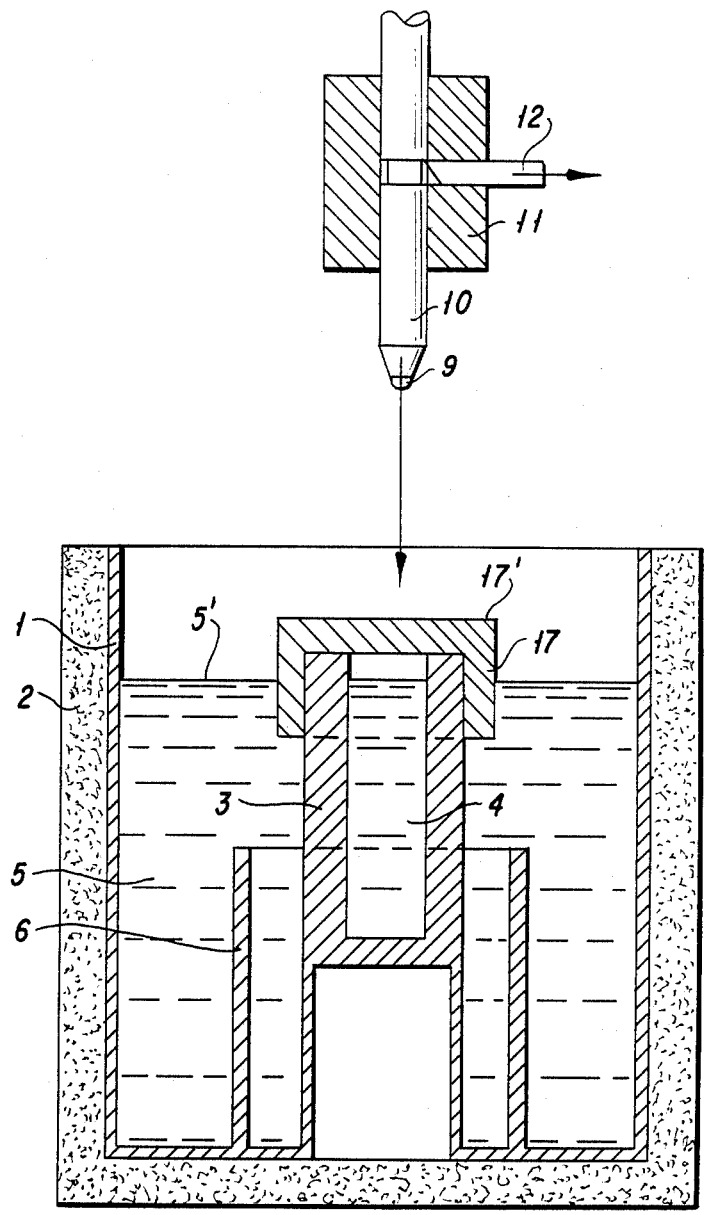
FIG. 3 is a diagrammatic cross-sectional view of apparatus in accordance with the invention for alternative cryofixation by immersion and on a metal mirror surface.

The different systems shown in FIG. 1 and FIG. 2 can be combined in a single apparatus in accordance with the invention as shown in FIG. 3, which apparatus is related to the apparatus of FIG. 1. For metal mirror surface cryofixation, a rotatable metallic member 17, having a top surface 17' polished to a high gloss and constituting the metal mirror surface, is simply superposed like a cover upon the metal tank 3 for the cooling medium 4. In so doing it is only necessary to ensure that the respective plane and cylindrical surfaces ensure good thermal contact. This may be achieved when the axes of the cylindrical surfaces are precisely perpendicular to the corresponding planar surface and the radii of the cylindrical surfaces differ only by an amount that enables the rotatable member 17 to be securely placed on and removed from the tank 3, taking into consideration the thermal expansion of the metals used.

Before carrying out a metal surface cryofixation, it is advantageous to raise the level of the $LH_2$ 5 above that shown in FIG. 1, so that the surface level of the $LN_2$ 5' (FIG. 3) lies above the top rim of sleeve 6 and the $LN_2$ 5' comes directly into contact with the rotatable metallic member 17, because in this way a minimum temperature in immediate proximity to the boiling point of $LN_2$, $-196°$ C., can be obtained. The illustrated combination according to the invention of a system for immersion cryofixation and a system for metal mirror surface cryofixation makes it possible to fix the same material successively by immersion into the cooling medium 4 and by application against the metal mirror surface 17', because it is unecessary to remove the refrigerant medium 4 from the system.

Figure 4C:
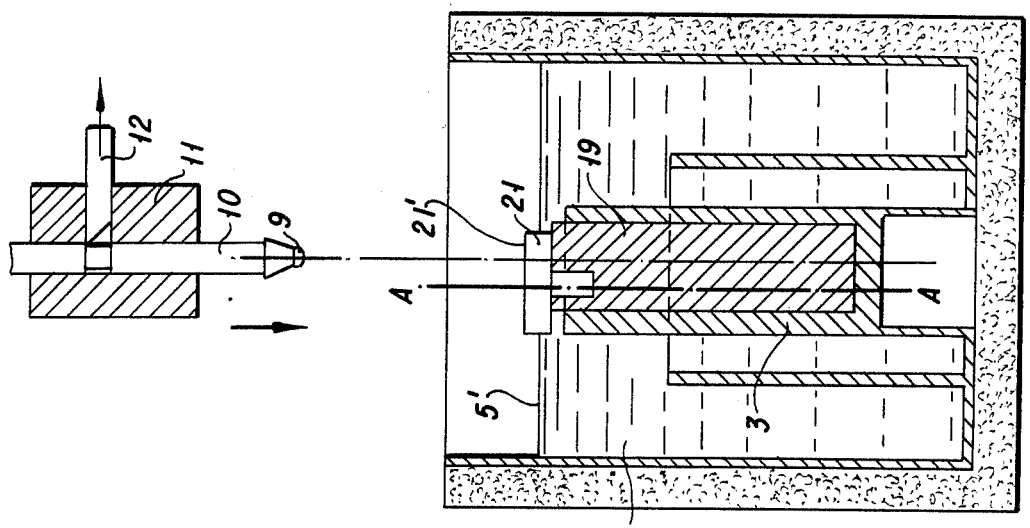
FIGS. 4a, 4b and 4c are diagrammatic cross-sectional views of further embodiments of apparatus in accordance with the invention.
Figure 4B:
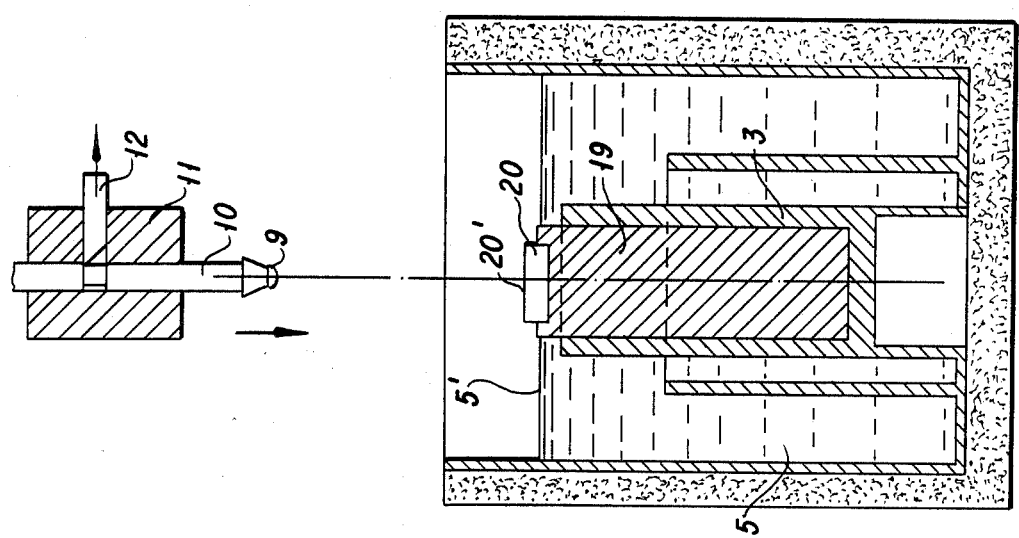
Figure 4A:
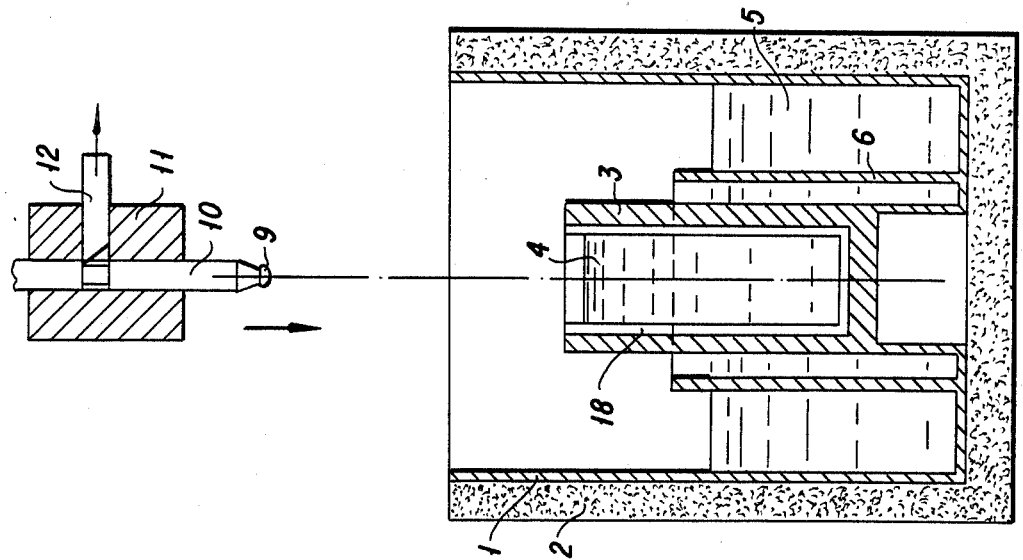

FIGS. 4a, 4b and 4c show further developments of apparatus according to the invention. FIG. 4a shows an embodiment which largely corresponds to FIG. 1 and permits immersion cryofixation. FIG. 4b shows the arrangement suitable for metal mirror surface cryofixation. In FIGS. 4a and 4b the refrigerant medium 4 is retained in a cylindrical tube 18 disposed in the tank 3; the tube 18 is exchangeable for a member having a mirror surface in the form of a cylindrical metal carrier 19 of the same dimensions. For alternating work the refrigerant liquid may be stored for subsequent immersion cryofixation in a pressure vessel or at low temperature in a suitable known manner.

By a convenient and advantageous development of the system shown in FIGS. 4a and 4b the metal mirror surface 20' may be situated not on the cylinder 19 itself, but on a small superposable or insertable element 20, which is exchangeable for an identical component after the completion of cryofixation.

Because the mirror surface frequently suffers somewhat during metal mirror cryofixation, such exchange permits work to be quickly continued, because the thermal capacity of the element 20 is so small in comparison to that of the tank 3 and that of the cylinder 19 carrying the element that cooling down to $LN_2$ temperature is complete within a very short time after the exchange. Further advantages of this arrangement are that polishing the metal mirror surface is simpler, that it is not necessary for the entire cylinder 19 to be manufactured from the specifically most favourable material, such as 99.999% Cu or Ag, and that the mirror can be coated or plated with a precious metal or with other particularly suitable layers, such as a Teflon coating, without excessive cost. As in the case of the apparatus shown in FIG. 3, it is convenient for metal mirror surface operation to raise the $LN_2$ 5 to a level 5' which brings the $LN_2$ into direct contact with at least the metal tank 3, and most preferably into direct contact with the mirror element 20, without flooding the mirror surface 20' with the $LN_2$ 5'.

Finally, FIG. 4c shows a variant of the apparatus in which a mirror plate 21 with a mirror surface 21' is arranged rotatably about an axis AA. Because this axis AA is located eccentrically parallel to the delivery axis and the axis of the injector rod 10, rotation of the plate 21 relative to the cylinder 19' or the tank 3 is sufficient to bring an absolutely clean and not previously used surface under the injector 10 for subsequent cryofixation.

Variations from the preferred embodiments shown in FIGS. 3 and 4 by way of example, and described above may be made within the scope of the invention without departing from the principles thereof. For example, the prinicples of the invention are not affected by the system for temperature adjustment, temperature regulation and temperature measurement, nor by the auxiliary apparatus for liquifying the refrigerant medium 4 or for recharging and regulating the level of the $LN_2$ 5 or 5'. The metal mirrors may be located on differently shaped and fastened elements and may be treated on their surfaces in different ways. The means of injecting the specimen and the contruction of the injector and the trigger, may also be modified.

I claim:

1. Apparatus for the mirror cryofixation by movement of a specimen along a delivery path of a liquid cryofixation device which comprises:
    a container for a cryogen;
    a tank, having an open top end for holding a cryofixation liquid, said tank being supported by said container on the delivery path for cooling by the cryogen; and
    a hollow, metallic member having a mirror surface on one end and sidewalls extending perpendicular to said one end, said metallic member being removably positionable on said open top end with a portion of said sidewalls being immersed in said cryogen;
    whereby a specimen may be cryofixed by contact with said mirror surface when said metallic member is positioned on said open end of said tank or, alternatively, cryofixed by immersion in the cryofixation liquid.

2. The apparatus according to claim 1 further including means to vary the level of cryogen in said container, whereby the level of liquid cryogen may be raised to contact said sidewalls.

3. The apparatus according to claim 1 wherein said tank and said hollow metallic member are cylindrical.

4. Apparatus according to claim 3 in which the mirror surface is rotatable about an axis parallel to, and spaced from, said delivery path.

5. The apparatus according to claim 3 wherein said metallic member is rotatable, whereby a fresh portion of said mirror surface may be presented to a subsequent specimen.

6. Apparatus according to claim 1, in which the tank is adapted to be cooled to a temperature below $-100°$ C. by the cryogenic refrigerant medium.

7. Apparatus according to claim 1, in which the mirror surface is substantially perpendicular to the delivery path.

8. Apparatus for the mirror cryofixation by movement of a specimen along a delivery path of a liquid cryofixation device, which comprises:
    a container for a cryogen;
    a tank having vertical sidewalls and an open top end for holding a cryofixation liquid, said tank being supported by said container on the delivery path for cooling by the cryogen;
    an elongated metallic member having sidewalls, said sidewalls being adapted to be in thermally conductive engagement with said vertical sidewall, when said metallic member is placed in said tank; and
    a mirror surface on the top end of said metallic member;
    whereby the cryofixation liquid may be replaced by said metallic member for mirror cryofixation of a specimen.

9. The apparatus according to claim 8 further including receptacle means for removing the cryofixation liquid from said tank, said receptacle means being adapted to be in thermally conductive engagement with said vertical sidewalls when said receptacle means is positioned in said tank.

10. The apparatus according to claim 9 wherein said metallic member, said tank and said receptacle means are cylindrical.

11. The apparatus according to claim 10 further including an end element, said end element having said mirror surface on one end thereof and a pin extending from the other end thereof, a bore in the top of said metallic member adapted to receive said pin, whereby said element provides interchangeable mirror surfaces for said metallic member.

12. The apparatus according to claim 11 wherein said bore is displaced from the center of said metallic member.

13. The apparatus according to claim 8 wherein said mirror surface is removable from said metallic member.

14. The apparatus according to claim 8 further including an end element, said end element having said mirror surface on one end thereof and a pin extending from the other end thereof, a bore in the top of said metallic member adapted to receive said pin, whereby said element provides interchangeable mirror surfaces for said metallic member.

15. The apparatus according to claim 14 wherein said bore is displaced from the center of said metallic member.

* * * * *